(12) United States Patent
Schultes et al.

(10) Patent No.: US 8,945,566 B2
(45) Date of Patent: Feb. 3, 2015

(54) METHODS FOR IMPROVING THE BIOACTIVITY OF THERAPEUTIC IGE ANTIBODIES FOR THE TREATMENT OF DISEASE

(75) Inventors: Birgit C. Schultes, Arlington, MA (US); Christopher F. Nicodemus, Charlestown, MA (US)

(73) Assignee: Quest PharmaTech, Inc., Alberta (CA)

( * ) Notice: Subject to any disclaimer, the term of this patent is extended or adjusted under 35 U.S.C. 154(b) by 0 days.

(21) Appl. No.: 13/456,492

(22) Filed: Apr. 26, 2012

(65) Prior Publication Data

US 2013/0058920 A1    Mar. 7, 2013

Related U.S. Application Data

(63) Continuation of application No. 12/900,251, filed on Oct. 7, 2010, now abandoned, which is a continuation of application No. PCT/US2009/040090, filed on Apr. 9, 2009.

(60) Provisional application No. 61/043,690, filed on Apr. 9, 2008, provisional application No. 61/044,581, filed on Apr. 14, 2008, provisional application No. 61/160,157, filed on Mar. 13, 2009.

(51) Int. Cl.
*A61K 39/395* (2006.01)
*A61K 39/00* (2006.01)

(52) U.S. Cl.
CPC ........... *A61K 39/0011* (2013.01); *A61K 39/395* (2013.01); *A61K 2039/555* (2013.01); *C07K 2317/52* (2013.01); *Y10S 424/805* (2013.01); *Y10S 530/862* (2013.01)
USPC .................. 424/155.1; 424/133.1; 424/141.1; 424/278.1; 424/805; 530/387.3; 530/387.9; 530/388.8; 530/862; 514/19.3

(58) Field of Classification Search
None
See application file for complete search history.

(56) References Cited

U.S. PATENT DOCUMENTS

| 7,795,379 B2 | 9/2010 | Jager et al. |
| 8,038,994 B2 | 10/2011 | Schultes et al. |
| 2005/0031619 A1 | 2/2005 | Nicodemus et al. |
| 2005/0271649 A1 | 12/2005 | Schultes et al. |
| 2006/0110746 A1 * | 5/2006 | Andre et al. ............... 435/6 |
| 2008/0044429 A1 | 2/2008 | Johnson et al. |
| 2008/0069832 A1 | 3/2008 | Chomez et al. |

FOREIGN PATENT DOCUMENTS

WO     WO 9211031 A1 *   7/1992

OTHER PUBLICATIONS

Buzdar et al., Clin Cancer Res. Jan. 1. 2007;13(1):228-33.*
Sigsgaard et al., J Clin Oncol. Apr. 1, 2001;19(7):2091-7.*
Stemmler et al., Clin Oncol (R Coll Radiol). Dec. 2005;17(8):630-5.*
Karagiannis, S.N., et al., "IgE-Antibody-Dependent Immunotherapy of Solid Tumors: Cytotoxic and Phagocytic Mechanisms of Eradication of Ovarian Cancer Cells," J. Immunology, 179(5): 2832-2843 (2007).
Miotti, S., et al., "Membrane association and shedding of the GPI-anchored Ca-MOv18 antigen in human ovary carcinoma cells," (abstract), International Journal of Cancer, 51(3): 499-505 (2006).
Wang, H. et al., "Structure and regulation of a polymorphic gene encoding folate receptor type γ/γ," Nucleic Acids Research, 26(9): 2132-2142 (1998).
Lynch, N. R., et al., "Passive Local Anaphylaxis: Demonstration of Antitumor Activity and Complementation of Intratumor BCG," J Natl Cancer Inst., 58(4): 1093-1098 (1977).
Hofmeister, V., et al., "Tumor stroma-associated antigens for anti-cancer immunotherapy," Cancer Immunol Immunother, 55:481-494 (2006).
Jain, Maneesh, et al., "Optimization of Radioimmunotherapy of Solid Tumors: Biological Impediments and Their Modulation," Clinical Cancer Research, 13(5):1374-1382 (2007).

* cited by examiner

*Primary Examiner* — Michael Szperka
(74) *Attorney, Agent, or Firm* — Elmore Patent Law Group, P.C.; Darlene A. Vanstone; Carolyn S. Elmore, Esq.

(57) ABSTRACT

The invention provides a method for increasing the bioactivity (e.g. the biosafety and efficacy) of a therapeutic IgE antibody of the invention in the treatment of a patient. Methods of the invention include: i) administering to the patient a therapeutic IgE antibody in combination with at least one bioactivity-enhancing agent, ii) strategic treatment regimens and protocols for the dosing and administration of a therapeutic IgE antibody of the invention, and iii) the use of a therapeutic IgE antibody having a variable region comprising at least one antigen binding region specific for binding an epitope of an antigen wherein the epitope is not highly repetitive or is non-repetitive.

8 Claims, 5 Drawing Sheets

METHODS FOR IMPROVING THE BIOACTIVITY OF THERAPEUTIC IGE ANTIBODIES FOR THE TREATMENT OF DISEASE

RELATED APPLICATIONS

This application is a continuation U.S. application Ser. No. 12/900,251, filed on Oct. 7, 2010, which is a continuation of International Application No. PCT/US2009/040090, which designated the United States and was filed on Apr. 9, 2009, published in English, which claims the benefit of U.S. Provisional Application Nos. 61/043,690, filed Apr. 9, 2008, 61/044,581, filed Apr. 14, 2008 and 61/160,157, filed on Mar. 13, 2009. The entire teachings of the above applications are incorporated herein by reference.

BACKGROUND OF THE INVENTION

The newly arising field of AllergoOncology is based upon observations and studies showing that those individuals with raised levels of IgE (e.g. individuals who suffer from allergies) are much less likely to suffer from certain types of cancer. Researchers in this field are exploring the therapeutic potential of the IgE antibody class in the prevention and treatment of certain cancers.

IgE antibodies mediate allergic and asthmatic reactions, characterized by immediate hypersensitivity, followed by an inflammatory delayed type response requiring the recruitment of effector cells. The uniqueness of the allergic reaction is due to the presence of mast cells and Langerhans/dendritic cells in the tissue that are sensitized by the IgE bound to the high-affinity FcεRI (Kinet, J P, *Annu. Rev. Immunol.*, 17:931-72: 931-972 (1999); and Ravetch J V, and Kinet J P, *Annu. Rev. Immunol.*, 9: 457-492 (1991)). The activated Langerhans/dendritic cells migrate to local lymph nodes and stimulate cognate T cells, which migrate to the tissue, participate in the inflammatory response and stimulate antibody synthesis. IgE bound to mast cells and basophils can cause degranulation of the cells, but it requires cross-linking by the antigen the IgE recognizes. Following the acute phase of recruitment, eosinophils are recruited in the late-phase reaction. Activated eosinophils are strong mediators of antibody-dependent cell-mediated cytotoxicity (ADCC) via toxic granule proteins and cause tissue damage via pro-inflammatory cytokines and vasoactive lipid mediators (leukotrienes, prostaglandin D2, platelet-activating factor). The processing of the IgE containing immune complex by Langerhans cells and dendritic cells is a critical step for the induction of the late-phase reaction. Activated T helper cells generate IL-4 and IL-5, which in turn recruits and activates eosinophils causing ADCC and antibody-dependent cell-mediated phagocytosis (ADCP) (Kinet, J P, *Annu. Rev. Immunol.*, 17:931-72: 931-972 (1999); Maurer, D., et al., *J. Immunol.*, 161: 2731-2739 (1998) and Maurer D., et al., *J. Immunol.*, 154: 6285-6290 (1995)).

While B cells can recognize antigen in its native conformation, T cells generally recognize antigen that has been "processed" by antigen presenting cells (APCs) and then presented on the surface of the cell by major histocompatibility complex (MHC) molecules (Peakman, M. and Vergani, D., New York: Churchhill Livingston; (1997)). MHC molecules are receptors for peptide antigens. There are two classes of MHC molecules, termed MHC class I and MHC class II. Although united in their function of peptide antigen presentation and contact points for T cells, the differences in the structure and intracellular trafficking of the two types are critical because among other things, they elicit very different immune responses. A major obstacle in the creation of effective tumor immunity is that typically, there is poor presentation of tumor antigen on MHC class I and class II molecules together (cross-presentation). Dendritic cells are bone marrow-derived leukocytes that are more potent initiators of T cell-dependent immune responses than any other antigen presenting cells that have been tested (Peakman, M. and Vergani, D., New York: Churchhill Livingston (1997)). Unlike other APCs, dendritic cells can acquire antigens from their environment and process them for cross-presentation, allowing activation of both $CD8^+$ and $CD4^+$ T cells. However, this process requires high antigen concentrations. Simultaneous presentation on MHC II provides for T helper cell activation. Depending on the stimuli, either production of cytokines IL-12 and IFN-γ by T helper (Th) cell 1 type and cytotoxic T-lymphocyte (CTL) induction occurs (collectively referred to herein as the "Th1/Tc1 immune response"); or IL-4, IL-5 and IL-10 is produced by Th2 cells for B cell help (referred to herein as "Th2 immune response"). An important factor in immune induction is the activation or maturation of the APC, which induces the expression of co-stimulatory molecules that are necessary to engage the T cell.

It is now believed that the engagement of the toll-like receptor (TLR) family (Okamoto, M. and Sato, M., *J. Med. Invest.*, 50: 9-24 (2003)) as well as other receptors including Fc receptors (Hamano, Y., et al., *J. Immunol.*, 164: 6113-6119 (2000) and Regnault, A., et al., *The Journal of Experimental Medicine*, 189: 371-380 (1999)) mediates activation and maturation of macrophages and dendritic cells, which is crucial for activating the innate immune system. Fc receptors have also been shown to facilitate antigen uptake and presentation. Among others, we have shown that immune complexed (IC)-pulsed dendritic cells induce stronger $CD4^+$ and $CD8^+$ T cell responses as compared to dendritic cells pulsed with PSA alone (Berlyn, K A, et al., *Clin. Immunol.*, 101: 276-283 (2001)). Similarly, NY-ESO-1 as well as ovalbumin or pyruvate dehydrogenase are all presented to T cells much more efficiently when captured as an immune complex rather than as free-antigen (Regnault A., et al., *The Journal of Experimental Medicine* 189:371-380 (1999); Nagata Y., et al., *Proc. Natl. Acad. Sci. U.S.A.*, 99: 10629-10634 (2002); Kita, H., et al., *J. Exp. Med.*, 195:113-123 (2002) and Schuurhuis, D H, et al., *J. Immunol.*, 168: 2240-2246 (2002)). The results suggest that effective cancer vaccines may be generated by administering antibodies that target circulating antigen and form immune complex that target dendritic cells in vivo.

IgE binds to two types of Fc receptors, called FcεRI (or high-affinity FcεR) ($K_a = 10^{11}$ $M^{-1}$) and FcεRII (or low-affinity FcεR, CD23) ($K_a < 10^8$ $M^{-1}$). Therefore, unlike antibodies of the IgG class, IgE binds to its FcεRI with extremely high affinity which in the case of FcεRI is about 3 orders of magnitude higher than that of IgG for the FcRs (FcγRI-III) and in the case of FcεRII is similar to the affinity of IgG for its high affinity FcγRI (Gould, H J, et al., *Annu. Rev. Immunol.*, 21: 579-628. Epub@2001 Dec@19.:579-628 (2003); Gounni, A S, et al., *Nature*, 367: 183-186 (1994); Kinet, J P, *Annu. Rev. Immunol.*, 17: 931-972 (1999) and Ravetch J V, and Kinet J P, *Annu. Rev. Immunol.*, 9: 457-492 (1991)). Because the IgE concentration in normal serum is usually very low (less than 1 µg/mL), the FcεR are typically available for occupancy if IgE is induced by allergies and parasitic infestation or if administered. The FcεRI is composed of four polypeptide chains, one α, one β, and two γ chains. The α chain contains the IgE binding site and is a member of the immunoglobulin supergene family. The FcεRII consists of one polypeptide chain which shows homology to animal lectin receptors. FcεRI is expressed on mast cells and basophils as well as Langerhans cells and dendritic cells where it is involved in antigen presentation, on eosinophils where it plays a role in defense against parasitic infection, and also on monocytes (see Kinet, J P, *Annu. Rev. Immunol.*, 17: 931-72:931-972 (1999) for a review). Crosslinking of the FcεRI receptors via bridging of bound IgE induces immediate release of mediators of inflammation such as histamine, various cationic proteases, leukotrienes, prostaglandin E2, or β-glucuronidase, and delayed secretion of IL-4, 5, and 6. FcεRII is a member of the Ig superfamily, more widely expressed on resting and mature B cells, monocytes, follicular dendritic cells, macrophages, eosinophils, platelets, Langerhans cells, and a subset of T cells (10-15% of tonsillar T cells). IL-4 up-regulates FcεRII expression on B cells and macrophages. FcεRII on macrophages, eosinophils, and platelets mediates ADCC to schistosomules, enhance phagocytosis, and induce the release of granule enzymes (Gounni, A S, et al., *Nature*, 367: 183-186 (1994); Kinet, J P, *Annu. Rev. Immunol.*, 17: 931-972 (1999) and Spiegelberg, H L, *J. Invest. Dermatol.*, 94: 49S-52S (1990)). FcεRII is involved in both IgE regulation and allergen presentation by B-cells, but understanding the functional roles of CD23 is further complicated by the fact that it exists both as a cell surface molecule and in a soluble form generated by cleavage from the cell surface; furthermore, it exists in both monomeric and oligomeric states (see Gould, H J, and Sutton, B J, *Nat. Rev. Immunol.*, 8:205-217 (2008) for a review). CD23 responds to high levels of IgE by downregulating IgE secretion. In human monocytes, CD23 triggering results in release of pro-inflammatory cytokines including tumor necrosis factor (TNF)-α, IL-1, IL-6, and granulocyte/macrophage-colony stimulating factor (GM-CSF). IL-4 appears to play a central role in immediate-type hypersensitivity. It induces human B cells to secrete IgE and IgG4 and activated T helper cells. IL-4 also stimulates mast cell growth and up-regulates FcεRII expression.

Most of the antibodies used in the treatment of cancer, including FDA approved antibodies such as trastuzumab (HERCEPTIN®) and rituximab (RITUXAN®)), are of the IgG class (Carter, P., IBC's Tenth International Conference. 6-9 Dec. 1999, La Jolla, Calif., USA. *IDrugs.* 3:259-261 (2000); Carter, P., *Nat. Rev. Cancer*, 1: 118-129 (2001) and Carter, P J, *Nat. Rev. Immunol.*, 6: 343-357 (2006)). However, four monoclonal IgE antibodies specific for tumor antigens have been reported. The application of IgE for the therapy of cancer was pioneered by Nagy et al. (Nagy, E., et al., *Cancer Immunol. Immunother.*, 34: 63-69 (1991)), who developed a murine IgE monoclonal antibody specific for the major envelope glycoprotein (gp36) of mouse mammary tumor virus (MMTV) and demonstrated significant anti-tumor activity in C3H/HeJ mice bearing a syngeneic MMTV-secreting mammary adenocarcinoma (H2712) (Nagy, E., et al., *Cancer Immunol. Immunother.*, 34: 63-69 (1991)). Kershaw et al. (Kershaw, M H, et al., *Oncol. Res.*, 10: 133-142 (1998)) developed a murine monoclonal IgE named 30.6, specific for an antigenic determinant expressed on the surface of colorectal adenocarcinoma cells. Mouse IgE 30.6 inhibited the growth of established human colorectal carcinoma COLO 205 cells growing subcutaneously in severe combined immune deficient (SCID) mice, although this effect was transient. By contrast, a mouse IgG 30.6 and a mouse/human chimeric IgE 30.6 did not show anti-tumor effects. The mouse IgE specific effect was attributed to the interaction of the antibody with FcεR bearing effector cells since the activity was specifically abrogated by prior administration of a non-specific mouse IgE (Kershaw, M H, et al., *Oncol. Res.*, 10: 133-142 (1998)). The lack of effect exhibited by the mouse/human chimeric IgE 30.6 is explained by the fact that mouse FcεRI binds mouse IgE, but not human IgE. Gould et al. (Gould, H J, et al., *Eur. J. Immunol.*, 29: 3527-3537 (1999)) developed a mouse/human chimeric IgE (MOv18-IgE) and IgG MOv18 (IgG1) specific for the ovarian cancer tumor associated antigen folate binding protein (FBP). The protective activities of MOv18-IgE and MOv18-IgG1 were compared in a SCID mouse xenograft model of human ovarian carcinoma (IGROV1). Mice were reconstituted with human peripheral blood mononuclear cells (PBMC) to provide the model with effector cells capable of binding human IgE constant regions. The beneficial effects of MOv18-IgE were greater and of longer duration than those of MOv18-IgG1 demonstrating the superior anti-tumor effects of IgE antibodies (Gould, H J, et al., *Eur. J. Immunol.*, 29: 3527-3537 (1999)). In addition, the group of Gould et al. recently demonstrated for the first time monocyte-mediated IgE-dependent tumor cell killing by two distinct pathways, ADCC and phagocytosis (ADCP), mediated through FcεRI and FcεRII (Karagiannis, S N, et al., *Cancer Immunol. Immunother.*, 57: 247-263 (2008) and Karagiannis, S N, et al., *J. Immunol.*, 179: 2832-2843 (2007)). This group has also used this assay system to make a preliminary assessment of bioactivity of an anti-Her2 IgE construct (Karragiannis, P., *Cancer Immunol and Immunother* (2008) epub ahead of print). Since human PBMC are short-lived in SCID mice the inventors have postulated that the anti-tumor effect will be enhanced in humans where the supply of effector cells would be permanent. None of the studies could address the capacity of the mouse/human chimeric IgE to elicit an adaptive immune response due to the fact that murine APCs such as dendritic cells do not express the FcεRI (Kinet, J P, *Annu. Rev. Immunol.*, 17: 931-72:931-972 (1999)).

Relevant epidemiological studies on the association of allergic diseases with cancer support a lower risk of cancer among people with a history of allergies or high levels of serum IgE including different hematopoietic malignancies (Grulich, A E and Vajdic, C M, *Pathology*, 37: 409-419 (2005); Wang, H. and Diepgen, T L, *Allergy*, 60: 1098-1111 (2005); Grulich, A E, et al., *Cancer Epidemiol. Biomarkers Prev.*, 16: 405-408 (2007); Turner, M C, et al., *Am. J. Epidemiol.*, 162: 212-221 (2005); Wang, H. and Diepgen, T L, Br., *J. Dermatol.*, 154: 205-210 (2006); Wang, H., et al., *Int. J. Cancer*, 119: 695-701 (2006); Turner, M C, et al., *Int. J. Cancer*, 118: 3124-3132 (2006) and Melbye, M., et al., J. *Natl. Cancer Inst.*, 99: 158-166 (2007)) and solid tumors such as ovarian, colorectal, pancreatic cancer, and glioma (Wang, H. and Diepgen, T L, *Allergy*, 60: 1098-1111 (2005); Turner, M C, et al., *Am. J. Epidemiol.*, 162: 212-221 (2005); Wang, H., et al., *Int. J. Cancer*, 119: 695-701 (2006); Turner, M C, et al., *Int. J. Cancer*, 118: 3124-3132 (2006); Mills, P K, et al., *Am. J. Epidemiol.*, 136: 287-295 (1992); Wiemels, J L, et al., *Cancer Res.*, 64: 8468-8473 (2004) and Wrensch, M., et al., *Cancer Res.*, 66: 4531-4541 (2006)).

Furthermore, mice infested with nematodes are resistant to syngeneic mammary adenocarcinoma and show lower incidence of spontaneous mammary tumors (Ogilvie, B M, et al., *Lancet.*, 1: 678-680 (1971) and Weatherly, N F, *J. Parasitol.*, 56: 748-752 (1970)). Eosinophilia, either in peripheral blood or tumor-associated tissue, is frequently associated with some tumor types and also found after immunotherapy with IL-2, IL-4, GM-CSF, and antibody to CTLA-4 (Lotfi, R, et al., *J. Immunother.*, 30: 16-28 (2007). Within several tumor types including gastrointestinal tumors, this observation is associated with a significantly better prognosis, whereas their presence in rejecting allografts is largely seen as a harbinger of poor outcome (Lotfi, R. and Lotze, M T, *J. Leukoc. Biol.*, 83: 456-460 (2008)). Matta et al. (*Clin Cancer Res* 13: 5348-

5354 2007) have reported that multiple myeloma patients with relatively higher IgE levels had a better survival than patients with lower levels of IgE. Importantly, this is clearly reflected on the levels of IgE and not the other classes of immunoglobulins. These studies are consistent with a natural role of IgE in the immunosurveillance of cancer including multiple myeloma. Fu, et al. (*Clin Exp Immunol* 153: 401-409 (2008)) demonstrated that antibodies of the IgE class isolated from pancreatic cancer patients mediate antibody-dependent cell-mediated cytotoxicity against cancer cells.

Finally, treatment with omalizumab (XOLAIR®), which decreases free IgE in serum and down-regulates IgE receptors in effector cells to dampen IgE-mediated inflammatory response, appears to lead to a higher chance of developing cancer. Approximately 1 in 200 treated asthmatic patients developed breast, prostate, melanoma, non-melanoma skin, or parotid gland malignancies during the median observation period of 1 year while in the control group the incidence was 1 in 500 (Dodig, S., et al., *Acta Pharm.*, 55: 123-138 (2005)). These studies suggest a natural role of IgE in the immunosurveillance of cancer.

The art has established methods to treat patients who have developed hypersensitivity reactions to chemotherapeutic agents as well as monoclonal antibodies used in the treatment of autoimmune disease and malignancy in which a rush desensitization to the therapeutic agent is performed (Castells et al., *J. Allergy Clin. Immunol.* (2008) 122:574). Castells describes a protocol that reduces immunogenicity to an IgG class therapeutic antibody by administering increasing amounts of subtherapeutic dosages to achieve desensitization to the IgG therapeutic over a 4-8 hour period. It is noteworthy that the typical starting concentration for a desensitization protocol with Rituxan is 0.034 mg/mL reflecting the high antibody doses required to achieve clinical effects with IgG1 class cancer targeting antibodies. The art does not address the use of IgE monoclonal antibodies as therapeutic agents or methods for mitigating hypersensitivity reactions when IgE monoclonals are used.

SUMMARY OF THE INVENTION

The invention provides methods for increasing the bioactivity (e.g. biosafety and/or efficacy) of a therapeutic IgE antibody in the treatment of a patient comprising administering to the patient a therapeutic IgE antibody in combination with at least one bioactivity-enhancing agent preferably selected from the group consisting of immunostimulatory compounds, chemotherapeutic agents, immunosuppressive agents, and any combination thereof, in an amount effective to increase the bioactivity of the therapeutic IgE antibody as compared to the bioactivity of the therapeutic IgE antibody when administered alone.

The invention further provides methods for increasing the bioactivity and particularly the biosafety of a therapeutic IgE antibody of the invention comprising administering to the patient a therapeutic IgE antibody of the invention comprising Fc epsilon (ε) constant regions and a variable region comprising at least one antigen binding region specific for binding an epitope of an antigen wherein the epitope is not highly repetitive or is non-repetitive.

The invention further provides methods for increasing the bioactivity of a therapeutic IgE antibody through the use of strategic treatment regimens and protocols for the dosing and administration of a therapeutic IgE antibody of the invention optionally in combination with at least one bioactivity enhancing agent. For example, the inventors are the first to appreciate that not only can therapeutic IgE antibodies be dosed in a much lower range than IgG antibodies, but also that the dosage range of a therapeutic IgE antibody which is effective to induce a potent direct IgE antibody mediated toxicity against the antigen and diseased cells is also effective for antigen processing, cross presentation and specific T cell stimulation of adaptive cellular immunity. The IgG therapeutic antibodies of the prior art lack this advantage. Typically the dosage of an IgG therapeutic antibody required to elicit the desired effector cell response against the target antigen is orders of magnitude higher than the dosage required for effective antigen cross presentation and T cell stimulation mediated by the IgG therapeutic antibody. Thus, what is considered the appropriate therapeutic dosage of a therapeutic IgG antibody is not the optimal dosage for also eliciting an antigen specific T cell response by the therapeutic IgG antibody and rather is inhibitory for antigen specific cross presentation and T cell stimulation. Monoclonal IgE can uniquely utilize effector cell mediated and specific T cell mediated immune pathways at a common dose.

The invention further provides methods for increasing the bioactivity, particularly the biosafety, of a therapeutic IgE antibody of the invention by enhancing the Th1-type immune response and CTL immune response (collectively referred to herein as the "Th1/Tc1" immune response) to an immune complex comprising an antigen and a therapeutic IgE antibody, comprising administering to the patient capable of mounting such Th1/Tc1 immune response, a therapeutic monoclonal IgE antibody optionally in combination with at least one bioactivity-enhancing agent.

DETAILED DESCRIPTION OF THE INVENTION

Figure 1:
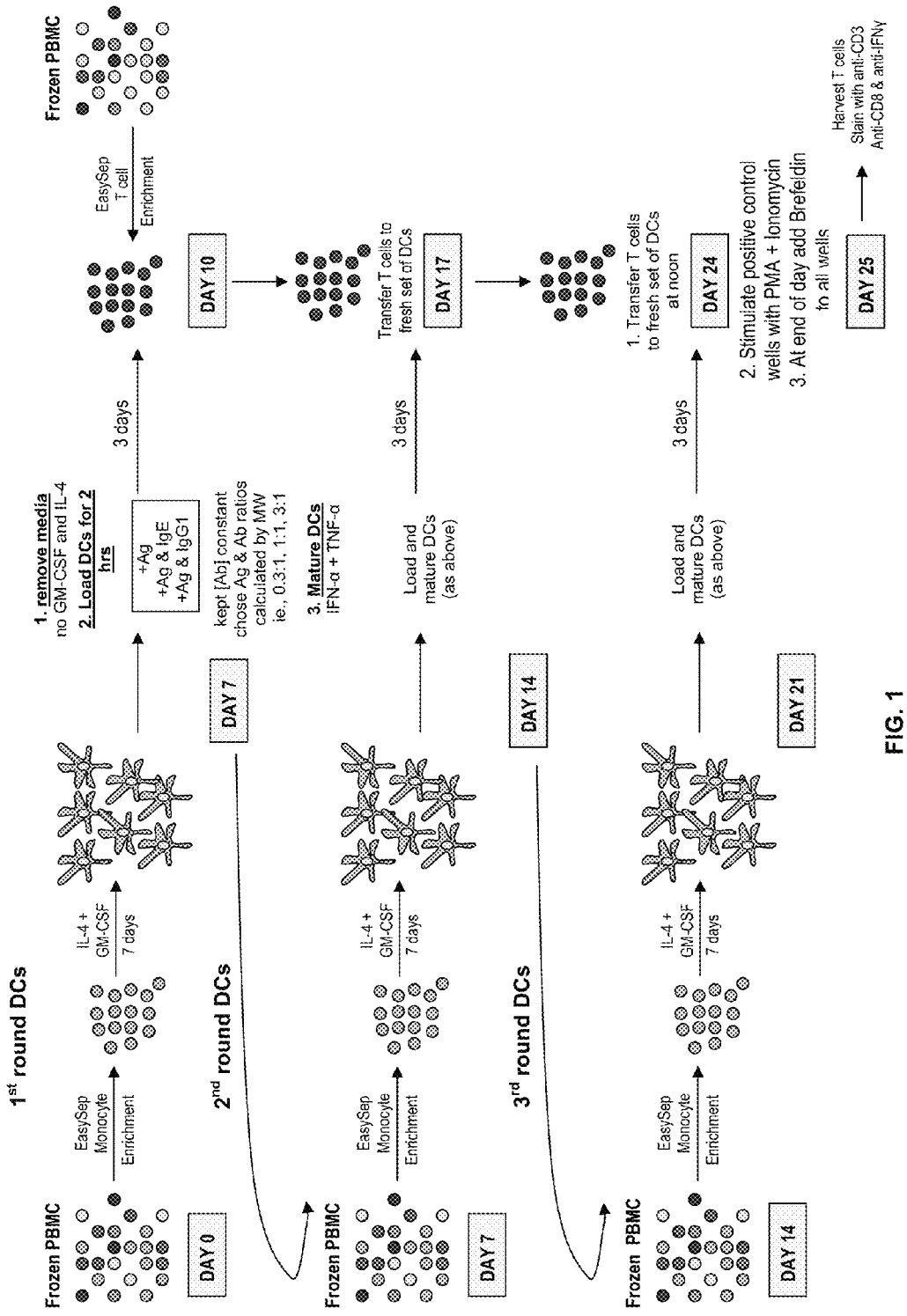
FIG. 1: schematic of antigen presentation assay (APA). Dendritic cells (DC) are cultured from human PBMCs in the presence of IL-4 and GM-CSF. On day 7, the primary culture is loaded with tumor associated antigen (TAA) and antibody (Ab) and matured with a standard maturation cocktail (e.g. TNF-α/IFN-α). Next, T cells are added and cultured for 7 days. Subsequently, the T cell culture is stimulated with two additional rounds of TAA/Ab using fresh DC cultures. Following the third round of TAA/Ab stimulation, the T cells are analyzed for tumor-specific responses.

The expectation that IgE will mediate potentially life threatening allergic reactions if infused into patients is the prejudice that currently exists in the state of the art. The present invention provides methods for improving the safety and bioactivity of IgE antibodies to direct hypersensitivity reactions for the purpose of controlling a disease state and altering antigen processing of disease specific antigens (e.g. tumor antigens and other antigen sources) while avoiding systemic hypersensitivity reactions.

While not be limited to any particular scientific theory, it is believed that monoclonal IgE antibodies of the invention are capable of directing hypersensitivity reactions by binding local disease related antigens either on the surface of the diseased tissue or in the microenvironment and bringing Fc epsilon R1 and R2 bearing effector cells including mast cells, basophils, macrophages and eosinphils to the site of a disease process (e.g. a micrometastatic focus of a malignant tumor), or the site of a chronic infection (e.g. tuberculin nodule, virally infected hepatocyte) inducing a local allergic inflammatory reaction with local cellular activation in the absence of systemic anaphylaxis.

It is also believed that IgE antibodies are capable of altering antigen processing to cancer and other diseases by binding disease associated antigen in circulation or at the site of a disease process (e.g. a tumor site) and being taken up through FCεRII mediated antigen processing; resulting in cross presentation of antigen peptide fragments in the context of MHC class I and MHC class II resulting in a robust cell mediated immune response including both CD4+ and CD8+ T cell activation, with a Tc1 dominance.

While the inventors have appreciated that both of these processes can be mediated by monoclonal IgE, despite the teaching of the art that would suggest a Th2 immune response would dominate; this effect can best be accomplished by careful selection of dose and administration of monoclonal IgE antibody and optionally with the selection and timing of co-administered agents to prevent systemic reactions to further boost the desired specific immune effector responses in the face of endogenous counter-regulatory pathways extant to limit autoimmunity. In one embodiment, antibodies comprising Fc epsilon (ε) constant regions and a variable region comprising at least one antigen binding region specific for an antigen (e.g. a cancer antigen), when optionally administered with an bioactivity-enhancing agent, will not only induce a Th2-type immune response to the antigen in a patient but will also enhance the Th1-type immune response to the antigen in a patient including enhancement of the CTL response and also the humoral immune response mediated by B cells. In one embodiment, the methods of the invention may induce shifting the dominant immune response in a patient from a Th2 to Th1 immune response (also referred to herein as "enhancing the Th1/Tc1 immune response"). The effect of such a shift would be to reduce the chance of immediate systemic hypersensitivity in a patient through in enrichment of IFN gamma antigen specific T cells and enhancement of cellular immune pathways. Additionally or alternatively, the methods of the invention may reduce or eliminate systemic hypersensitivity by reducing vigor of crosslinking of Fcε receptors via the choice of non repetitive epitope targets in the production of IgE and/or through precise co-medication to prevent the elicitation of allergic inflammatory histamine releasing factors that promote systemic not limited local immediate hypersensitivity reactions (mast cell degranulation).

A "therapeutic IgE antibody" is an antibody comprising Fc epsilon (ε) constant regions and a variable region comprising at least one antigen binding region specific for an antigen (e.g. a cancer antigen), that can bind to an antigen on a target cell or in circulation to cause a therapeutic effect in a patient. In one embodiment, the antigen is not an allergen or other antigen that is the normal physiological target of unmodified IgE present in the subject. In a preferred embodiment, the therapeutic IgE antibody is a monoclonal antibody.

The terms "monoclonal antibody" or "monoclonal antibodies" as used herein refer to a preparation of antibodies of single molecular composition. A monoclonal antibody composition displays a single binding specificity and affinity for a particular epitope. The monoclonal antibodies of the present invention are preferably chimeric, humanized, or fully human in order to bind human Fc epsilon receptors when the subject host is a human. Humanized and fully human antibodies are also useful in reducing immunogenicity toward the murine components of, for example, a chimeric antibody, when the host subject is human. Methods for producing monoclonal antibodies are well known in the art.

In one preferred embodiment, the therapeutic IgE antibody is a chimeric monoclonal antibody. The term "chimeric monoclonal antibody" refers to monoclonal antibodies displaying a single binding specificity which have one or more regions derived from one antibody and one or more regions derived from another antibody. In a preferred embodiment of the invention, the constant regions are derived from human Fc epsilon (ε) (heavy chain) and human kappa or lambda (light chain) constant regions. The variable regions of a chimeric antibody may be of human or non-human origin but are typically of non-human origin. In one embodiment, the variable region is of non-human origin such as from rodents, for example, mouse (murine), rabbit, rat or hamster. In one embodiment, the variable region is of murine origin. Previously published methodology used to generate mouse/human chimeric or humanized antibodies that has yielded the successful production of various human chimeric antibodies or antibody fusion proteins (Helguera G, Penichet M L., *Methods Mol. Med.* 109:347-74 (2005)). Other methods for producing chimeric antibodies are well known in the art.

As used herein, "humanized" monoclonal antibodies comprise constant regions are derived from human Fc epsilon (ε) (heavy chain) and human kappa or lambda (light chain) constant regions. The variable regions of the antibodies preferably comprise a framework of human origin and antigen binding regions of non-human origin.

Fully human or human-like antibodies may be produced through vaccination of genetically engineered animals such as mouse lines produced at Abgenix (CA) and MedaRex (NJ) which contain the human immunoglobulin genetic repertoire and produce fully human antibodies in response to vaccination. Further, the use of phage display libraries incorporating the coding regions of human variable regions which can be identified and selected in an antigen screening assay to produce a human immunoglobulin variable region binding to a target antigen.

In one embodiment, the therapeutic IgE antibody is not a chimeric antibody comprising a human Fcε constant region and mouse variable region having an antigen binding region that is specific for an epitope of HER2 (which binds the epitope of HER2 defined by the antibody contained in Herceptin) or an antigen binding region that is specific for an epitope of CD20 (which binds the epitope of CD20 that is defined by the antibody contained in Rituximab) or an antigen which binds an epitope specific for an antibody disclosed in U.S. Pat. No. 5,977,322.

The term "antigen binding region" refers to that portion of an antibody of the invention which contains the amino acid residues that interact with an antigen and confer on the antibody its specificity and affinity for the antigen. The antibody region includes the "framework" amino acid residues necessary to maintain the proper confirmation of the antigen binding residues.

An "antigen" is a molecule or portion of a molecule capable of being bound by an antibody which is additionally capable of inducing an animal to produce antibody capable of binding to an epitope of that antigen. In one embodiment, the antigen is capable of being bound by an IgE antibody of the invention to form an immune complex that is capable of inducing a specific IgE-mediated immune response to the antigen in a patient capable of mounting such immune response. As used herein, a "patient capable of mounting (the referenced) immune response" is a subject such as a human patient or other animal subject with functional T-cells, mast cells, basophils, eosinophils, monocytes, macrophages and dendritic cells with receptor affinity for the administered IgE antibody of the invention as distinguished from non-human animal models, for example, whose immune systems do not contain Fc epsilon receptors capable of binding human IgE permitting generation of functional T-cells, mast cells, eosinophils and dendritic cells in response to the administered antibody.

Preferred antigens include any soluble antigen that is detectable in body fluid (e.g. blood serum ascites, saliva or the like). In one preferred embodiment, the antigen is a tumor associated antigen (TAA). In one embodiment, the antigen, on its own, may not be capable of stimulating an immune response or elicits only a weak immune response for any number of reasons, for example, the antigen is a "self" antigen, not normally recognized by the immune system as requiring response or the immune system has otherwise become tolerant to the antigen and does not mount an immune response.

An antigen can have one or more epitopes that are the same or different. In one embodiment, the antibodies of the invention are specific for a single, non-repetitive epitope of the antigen. Thus, the immune complex formed by an antibody of the invention and its antigen is referred to as "monovalent" in that only one antibody of the invention may be bound to a single molecule of antigen at any one time.

The term "epitope" is meant to refer to that portion of any molecule capable of being recognized by and bound by an antibody at one or more of the antibody's binding regions. Epitopes generally comprise chemically active surface groupings of molecules such as amino acids or sugar side chains and have specific three dimensional structure characteristics as well as specific charge characteristics. The term "non-repetitive epitope" means that only one such epitope is present in the antigen. An epitope that is not "highly repetitive" means an epitope whose frequency and configuration upon the antigen are such that when an immune complex is formed between the therapeutic IgE antibody and the antigen, such immune complex does not cause crosslinking of the Fcε receptors on dendritic cells or other relevant APCs.

An "immune complex" (IC) is a complex formed by an antibody and its target antigen. An immune complex may be "polyvalent" meaning that more than one antibody is associated with an antigen, or "multimeric" meaning that multiple antigens and antibodies are complexed together, or "monovalent" meaning that each antigen molecule is bound to only one antibody molecule.

The term "cancer antigen" as used herein can be any type of cancer antigen known in the art. The cancer antigen may be an epithelial cancer antigen, (e.g., breast, gastrointestinal, lung), a prostate specific cancer antigen (PSA) or prostate specific membrane antigen (PSMA), a bladder cancer antigen, a lung (e.g., small cell lung) cancer antigen, a colon cancer antigen, an ovarian cancer antigen, a brain cancer antigen, a gastric cancer antigen, a renal cell carcinoma antigen, a pancreatic cancer antigen, a liver cancer antigen, an esophageal cancer antigen, a head and neck cancer antigen, or a colorectal cancer antigen. A cancer antigen can also be a lymphoma antigen (e.g., non-Hodgkin's lymphoma or Hodgkin's lymphoma), a B-cell lymphoma cancer antigen, a leukemia antigen, a myeloma (i.e., multiple myeloma or plasma cell myeloma) antigen, an acute lymphoblastic leukemia antigen, a chronic myeloid leukemia antigen, or an acute myelogenous leukemia antigen. Other cancer antigens include but are not limited to mucin-1 protein or peptide (MUC-1) that is found on all human adenocarcinomas: pancreas, colon, breast, ovarian, lung, prostate, head and neck, including multiple myelomas and some B cell lymphomas; mutated B-Raf antigen, which is associated with melanoma and colon cancer; human epidermal growth factor receptor-2 (HER-2/neu) antigen; epidermal growth factor receptor (EGFR) antigen associated lung cancer, head and neck cancer, colon cancer, colorectal cancer, breast cancer, prostate cancer, gastric cancer, ovarian cancer, brain cancer and bladder cancer; prostate-specific antigen (PSA) and/or prostate-specific membrane antigen (PSMA) that are prevalently expressed in androgen-independent prostate cancers; is Gp-100 Glycoprotein 100 (gp 100) associated with melanoma carcinoembryonic (CEA) antigen; carbohydrate antigen 10.9 (CA 19.9) related to the Lewis A blood group substance and is associated with colorectal cancers; and a melanoma cancer antigen such as MART-1.

In one preferred embodiment, the invention provides methods of increasing the bioactivity of a therapeutic IgE monoclonal antibody in a patient comprising administering a therapeutic IgE monoclonal antibody of the invention in combination with a bioactivity enhancing agent in an amount effective to increase the bioactivity of the IgE monoclonal antibody as compared to the bioactivity of the IgE antibody when administered alone. The term "bioactivity-enhancing agent" refers to an agent preferably selected from the group consisting of immunostimulatory compounds, chemotherapeutic agents, anti-cancer antibodies and anti-inflammatory agents, in an amount able to increase the bioactivity of the therapeutic IgE antibody as compared to the bioactivity of the therapeutic IgE antibody when administered alone. "Increasing the bioactivity of a therapeutic IgE antibody" is meant to refer to any one or more of the following outcomes favorably impacting the therapeutic index of the IgE antibody when administered to a patient in vitro or in vivo (in an appropriate animal system) or ex vivo suffering from a disease (e.g. cancer) associated with the expression of an antigen targeted by an IgE antibody of the invention, or when used in a preclinical model of such a clinical circumstance: (i) reduction in tumor size, (ii) extension of time to tumor progression, (iii) extension of disease- or tumor-free survival, (iv) increase in overall survival, (v) reduction of the dosage of the antibody, (vi) reduction of the rate of disease progression, (vii) increased amelioration of disease symptoms, (viii) reduction in the frequency of treatment, (ix) reduction or elimination of the occurrence of systemic hypersensitivity in a patient, (x)

enhancement of a Th1 type immune response in a patient, (xi) enhancement of CTL immune response in a patient, (xii) reduction in allergic responses to the therapeutic IgE antibody, (xiii) reduction or inhibition of non-IgE mediated factors that participate in allergic responses to the therapeutic IgE antibody, (xiv) activating T cells, (xv) eliciting ADCC and ADCP immune responses in a patient capable of mounting such a response, (xvi) mobilizing the use of macrophage, monocyte, eosinophil, basophil, and mast cells as effector cells (xvii) inducing local hypersensitivity reactions including ADCC, ADCP, and CTL responses at the site of the tumor or in the tumor microenvironment in a patient capable of mounting such a response. In certain embodiments, increased bioactivity is compared to the bioactivity (e.g., the predicted or measured bioactivity using appropriate pre-clinical models) of the therapeutic IgE antibody used in a treatment without a compound (i.e. a bioactivity enhancing agent) of the invention.

In one preferred embodiment, the invention provides methods of increasing the biosafety of a therapeutic IgE monoclonal antibody in a patient comprising administering a therapeutic IgE monoclonal antibody of the invention in combination with a bioactivity enhancing agent in an amount effective to increase the biosafety of the IgE monoclonal antibody as compared to the biosafety of the IgE antibody when administered alone. The term "increasing the biosafety" of an therapeutic IgE antibody means any one or more of the following outcomes: (i) reduction of the dosage of the antibody, (ii) reduction in the frequency of treatment, (iii) reduction or elimination of the occurrence of systemic hypersensitivity in a patient, (iv) induce shifting the dominant immune response in a patient from a Th2 to Th1 immune response; (v) reduction or inhibition of non-IgE mediated factors that participate in allergic responses to the therapeutic IgE antibody. In certain embodiments, increased biosafety is compared to the biosafety (e.g., the predicted or measured biosafety using appropriate preclinical models) of the therapeutic IgE antibody used in a treatment without a compound (i.e. a bioactivity enhancing agent) of the invention.

In one embodiment, at least one bioactivity enhancing agent is an immunostimulatory compound. Exemplary immunostimulatory compounds include toll-like receptor (TLR) agonists (e.g., TLR3, TLR4, TLR7, TLR9), N-acetyl-muramyl-L-alanine-D-isoglutamine (MDP), lipopolysaccharides (LPS), genetically modified and/or degraded LPS, alum, glucan, colony stimulating factors (e.g., EPO, GM-CSF, G-CSF, M-CSF, pegylated G-CSF, SCF, IL-3, IL6, PIXY 321), interferons (e.g., .gamma.-interferon, .alpha.-interferon), interleukins (e.g., IL-2, IL-7, IL-12, IL-15, IL-18), MHC Class II binding peptides, saponins (e.g., QS21), unmethylated CpG sequences, 1-methyl tryptophan, arginase inhibitors, cyclophosphamide, antibodies that block immunosuppressive functions (e.g., anti-CTLA4 antibodies, anti-TGF-beta, etc.), and mixtures of two or more thereof.

In one preferred embodiment the immunostimulatory compound is a TLR3 agonist. In preferred embodiments, the TLR3 agonist for use according to the invention is a double stranded nucleic acid selected from the group consisting of: polyinosinic acid and polycytidylic acid, polyadenylic acid and polyuridylic acid, polyinosinic acid analogue and polycytidylic acid, polyinosinic acid and polycytidylic acid analogue, polyinosinic acid analogue and polycytidylic acid analogue, polyadenylic acid analogue and polyuridylic acid, polyadenylic acid and polyuridylic acid analogue, and polyadenylic acid analogue and polyuridylic acid analogue. Specific examples of double-stranded RNA as TLR3 agonists further include Polyadenur (Ipsen) and Ampligen (Hemispherx). Polyadenur is a polyA/U RNA molecule, i.e., contains a polyA strand and a polyU strand. Ampligen is disclosed for instance in EP 281 380 or EP 113 162.

In one embodiment the immunostimulatory compound is a TLR4 agonist. Exemplary TLR4 agonists include taxanes such as paclitaxel and docetaxal, lipopolysaccharides (LPS); *E. coli* LPS; and *P. gingivalis* LPS.

In one preferred embodiment, the bioactivity-enhancing agent is a chemotherapeutic agent. Exemplary chemotherapeutic agents of the present invention can include one or more further chemotherapeutic agents selected from the group consisting of nitrogen mustards (e.g., cyclophosphamide and ifosfamide), aziridines (e.g., thiotepa), alkyl sulfonates (e.g., busulfan), nitrosoureas (e.g., carmustine and streptozocin), platinum complexes (e.g., carboplatin and cisplatin), non-classical alkylating agents (e.g., dacarbazine and temozolamide), folate analogs (e.g., methotrexate), purine analogs (e.g., fludarabine and mercaptopurine), adenosine analogs (e.g., cladribine and pentostatin), pyrimidine analogs (e.g., fluorouracil (alone or in combination with leucovorin) and gemcitabine), substituted ureas (e.g., hydroxyurea), antitumor antibiotics (e.g., bleomycin and doxorubicin), epipodophyllotoxins (e.g., etoposide and teniposide), microtubule agents (e.g., docetaxel and paclitaxel), camptothecin analogs (e.g., irinotecan and topotecan), enzymes (e.g., asparaginase), cytokines (e.g., interleukin-2 and interferon-.alpha.), monoclonal antibodies (e.g., trastuzumab and bevacizumab), recombinant toxins and immunotoxins (e.g., recombinant cholera toxin-B and TP-38), cancer gene therapies, physical therapies (e.g., hyperthermia, radiation therapy, and surgery) and cancer vaccines (e.g., vaccine against telomerase).

In one embodiment, at least one bioactivity-enhancing agent is an immunosuppressive agent including, but not limited to, cyclosporine, azathioprine, mycophenolic acid, mycophenolate mofetil, corticosteroids (e.g., cortisol, or prednisone), methotrexate, gold salts, sulfasalazine, antimalarials, brequinar, leflunomide, mizoribine, 15-deoxyspergualine, 6-mercaptopurine, cyclophosphamide, rapamycin, tacrolimus (FK-506), OKT3, anti-thymocyte globulin. In accordance with the invention, immunosuppressive agents include one or more immunosuppressive antibodies (e.g., antibodies against MHC, CD2, CD3, CD4, CD7, CD28, B7, CD40, CD45, IFN-.gamma. TNF-.alpha., IL-4, IL-5, IL-6R, IL-7, IL-8, IL-10, CD11a, CD20, or CD58, or antibodies against their ligands) and other immunomodulatory compounds (e.g., soluble IL-15R or IL-10). Preferred immunosuppressive agents include cortocosteriods.

In one embodiment, the invention provides a method for increasing the bioactivity, particularly the biosafety of an IgE antibody of the invention comprising enhancing the Th1/Tc1 immune response to an immune complex comprising an antigen and an IgE antibody in a patient, preferably a human patient capable of mounting such Th1/Tc1 immune response, comprising administering to the patient a therapeutic monoclonal IgE antibody of the invention optionally in combination with at least one bioactivity-enhancing agent preferably selected from the group consisting of: immunostimulatory compounds, chemotherapeutic agents, immunosuppressive agents, and any combination thereof, in an amount effective to enhance the patient's Th1/Tc1 response (e.g. a CD4, CD8 CTL, IFN gamma associated cellular response) to the immune complex. The effect of a primary CD8 CTL response would be to mediate anti-tumor effects with reduced tendency to induce clinically worrisome immediate hypersensitivity in a patient such as systemic anaphylaxis. As used herein the term "enhancing" includes switching the dominant immune response in a subject from a Th2 response to a Th1 response.

In one embodiment, the invention provides a method for increasing the bioactivity, particularly the biosafety of an IgE antibody of the invention comprising administering to the patient a therapeutic IgE antibody of the invention comprising Fc epsilon ($\epsilon$) constant regions and a variable region comprising at least one antigen binding region specific for binding an epitope of an antigen wherein the epitope is not highly repetitive or is non-repetitive optionally in combination with a bioactivity enhancing agent. Additionally or alternatively, the methods of the invention may reduce or eliminate systemic hypersensitivity by reducing or eliminating crosslinking of Fc$\epsilon$ receptors which is the cause of mast cell or basophil degranulation. Systemic reactions such as systemic anaphylaxis are generally associated with a polyclonal IgE response, and production of T cell derived mast cell activating factors that permit a local reaction to become systemic. Systemic reactions are associated with the vigorous crosslinking associated with a multi-epitopic polyclonal IgE response. Immune complexes comprising antigen an in combination with an IgE antibody of the invention to a non-repetitive epitope of the antigen will be less likely to crosslink Fc$\epsilon$Rs to the level of systemic symptoms when bound to mast cells or granulocytes in circulation than compared to antigen specific polyclonal IgE.

Therefore, the invention also provides methods of reducing systemic hypersensitivity in a patient being treated with a therapeutic IgE antibody comprising administering to the patient a therapeutic IgE monoclonal antibody of the invention comprising at least one antigen binding region specific for binding an epitope, preferably of an antigen wherein the epitope is not highly repetitive or is non-repetitive, optionally in combination with at least one bioactivity-enhancing agent selected from the group consisting of: immunostimulatory compounds, chemotherapeutic agents, immunosuppressive agents, and any combination thereof, in an amount effective to reduce systemic hypersensitivity in a patient as compared to the administration of the therapeutic IgE antibody alone.

Currently the state of the art teaches that when immune complexes consisting of antigen and polyclonal IgE antibodies or IgE antibodies to a multi-epitopic allergen bind to antigen presenting cells in atopic individuals as well as to mast cells or basophils, the FcϵR would be crosslinked, which leads to cellular activation, local cytokine production favoring a Th2 biased immune response, activation of T helper 2 (Th2) cells, and secretion of interleukin (IL)-4 and IL-5. Thus the art expects that the cytokines will subsequently induce Th2 immunity and lead to allergic inflammation including recruitment and activation of eosinophils and other allergic inflammatory cells. Maurer, D., et al., *J. Immunol.,* 161: 2731-2739 (1998) and Maurer D., et al., *J. Immunol.,* 154: 6285-6290 (1995). The art does not address immunity in a circumstance where the antigen is self tumor antigen and not an allergen.

However, the inventors have found that when immune complexes consisting of antigen and monoclonal IgE antibodies to a tumor antigen epitope are bound by dendritic cells derived from a non atopic patient in an in vitro cell culture system, the dendritic cells express primarily Fcϵ RII and produce a T cell stimulation to the antigen that has characteristics of a Th1/Tc1 immune response, with prominent induction of IFN-gamma producing CD4 and CD8 antigen specific lymphocytes. Of particular importance is the generation through this mechanism of specific and protective CD8 IFN-gamma positive cytotoxic T-lymphocytes (CTLs) response against the antigen which will cause lysing of tumor cells or at metastatic sites that express the tumor antigen in context of MHC class I.

IgE mediated mast cell and local basophil activation will result in a local reaction that is measurable quantitatively with acute measurement of the ensuing wheal and flare reaction (allergen skin test) in humans or rodents and other higher organisms. The immediate skin test reaction is only marginally inhibited in the presence of an acute dose of corticosteroid and reflects local vascular leak and increased local blood flow in response to histamine, prostaglandin, leukotriene, and other acute mediators released form the allergic effector cells. Additional late allergic symptoms also occur (Macguire, Nicodemus, *Clin Immun* 1999) (Norman et al, *Am J Resp Crit care Med,* 1996) as observed following administration of T cell epitope enriched, but non IgE reactive peptides. Although the factors that definitively mediate these reactions have yet to be established in the Art, they are not IgE mediated. Without being limited to any one theory, it is believed therefore that inhibition of non-IgE mediated systemic factors that play a role in the allergic immune response using a bioactivity enhancing agent in combination with an IgE antibody in accordance with the invention would result in the dampening of systemic hypersensitivity while preserving local IgE mediated allergic immune response against an antigen. Thus it is possible to use monoclonal IgE as a safe and highly bioactive therapy to induce specific immunity, mediate targeted cell killing, and provide a new modality for the treatment of malignancy.

The expectation and teaching of immunotherapist has been that corticosteroid administration is immune suppressive, as is cytotoxic chemotherapy administration; and therefore clinically effective immunotherapy should be given remote from such interventions. Recently the inventors (Braly, Nicodemus, et al, *JIT* 2009) have demonstrated that concomitant corticosteroid and paclitaxel/carboplatin administration can be immune enhancing in inducing immunity with intravenously administered xenotypic IgG to a tumor antigen in ovarian cancer patients. In addition they reported that the schedule of component administration importantly impacts the kinetics and magnitude of the immune responses. By extension, the safe and effective administration of a therapeutic monoclonal IgE to a target antigen can be accomplished through premedication with a corticosteroid 8 hours to 30 minutes prior to antibody infusion. While local reactions at the site of pathology will occur; and late cellular immunity induced through uptake of IgE/antigen by antigen presenting cells systemic anaphylaxis will be avoided. The clinical effect can be further potentiated by following the antibody administration 1 to 8 hours later with the infusion of a specific immune adjuvant, preferably a TLR agonist. In the treatment of malignancy, acute cytotoxic agents can be administered concurrently, although as the pharmacology of specific cancer treatments varies, and advances in cancer treatment must start with standard of care interventions, the cancer specific interventions must be customized empirically.

The methods of the invention also comprise increasing the bioactivity of a therapeutic IgE antibody of the invention through the use of strategic dosing and/or administration protocols. For example, the inventors are the first to appreciate that not only can therapeutic IgE antibodies be dosed in a much lower range than IgG antibodies currently in typical clinical use as cancer therapies, but also that the dosage range of a therapeutic IgE antibody which is effective to induce a potent direct IgE antibody mediated toxicity against the antigen and diseased cells is also effective for antigen processing, cross presentation and antigen specific T cell stimulation resulting in a Th1 cell mediated response (e.g. a CD4, CD8 CTL, IFN gamma associated cellular response). The IgG therapeutic antibodies of the prior art lack this advantage.

Typically the dosage of an IgG therapeutic antibody required to elicit the desired effector cell response against the target antigen is orders of magnitude higher than the dosage needed for antigen cross presentation and antigen specific T cell stimulation mediated by the IgG therapeutic antibody. Thus, what is considered the appropriate therapeutic dosage of a therapeutic IgG antibody is not the optimal dosage for also eliciting a T cell response by the therapeutic IgG antibody (and if fact is considered a dosage that is likely to inhibit any T cell response to the antigen) thereby eliminating the T cell mediated pathway of defense by the immune system in the treatment of diseases related to the target antigens. Monoclonal IgE can uniquely utilize direct effector cell mediated and specific T cell mediated immune pathways at a common dose. As is used herein the phrase "direct IgE antibody mediated toxicity against the antigen and diseased cells" means an immune response involving direct targeting of antigen bearing cells such as ADCC immune responses, ADCP immune responses or both ADCC and ADCP immune responses against the antigen/IgE immune complex as evidenced by the stimulation of eosinophils, mast cells, basophils and other cells to release pro-inflammatory cytokines, proteases and vasoactive lipid mediators (e.g. leukotrienes, prostaglandin D2, and platelet activating factor) when bound to the antigen/IgE immune complex via IgE antibody receptors FcϵRI and FcϵRII.

Therefore, the invention provides methods of increasing the bioactivity of a therapeutic IgE antibody comprising the step of administering an IgE antibody to a patient in an amount effective to induce direct mast cell, basophil, eosinophil effector cell targeting of the antigen disease site and T-cell mediated cellular immune response to the antigen in a patient capable of mounting such responses.

In another example of increasing the bioactivity and biosafety of a therapeutic IgE antibody of the invention, the rate of administration in combination with the route of administration can play a significant role in increasing the biosafety of an antibody of the invention. For example, in one embodiment, intravenous administration at a concentration of 0.010 to 0.1 mg/ml at a rate of 1 to 4 ml/min for 30 minutes is believed to increase the biosafety of the therapeutic IgE antibody of the invention for the reasons discussed below.

In another example, the monoclonal IgE antibody may administered intravenously, subcutaneously interarterially or intraperitoneally depending on the clinical condition of the patient and the location of the disease process. Direct interarterial administration of the IgE may also be considered, to assure maximal perfusion of a tumor with the monoclonal IgE antibody, recognizing that IgE will rapidly clear from the circulation through the binding of antigen by the antigen-binding region of the antibody and the binding of effector cells bearing CD23 and FcϵR1. In the case of micro metastatic disease the intravenous route is generally preferred although in the case of ovarian or other intra-abdominal cancers, intraperitoneal administration is also a viable strategy to enhance bioactivity of the IgE antibody in treating metastatic disease.

The administration of the therapeutic IgE antibody can be further enhanced through the pre-administration of a corticosteroid (e.g. cortisol 50 mg or methyl prodisolone 20 mg) 8 hours to 30 minutes prior to the IgE antibody infusion. While not interfering with acute immune stimulatory effects of the antibody administration, the corticosteroid will reduce the likelihood and severity of any systemic signs and symptoms associated with the monoclonal IgE infusion.

Bioactivity is further enhanced by concurrent day administration of paclitaxel or docetaxel as well as liposomal doxorubicin. For Gemcitabine Bioactivity is enhanced by administration of the gemcitabine 1 to 4 days prior to antibody infusion. Chemotherapeutics are to be administered according to standard dosing protocols for the treatment standards of specific malignant conditions. Other cytotoxic agents may be administered according to schedules that must be customized to the clinical case under consideration.

Bioactivity and be further enhanced through the scheduled administration of immune enhancing agents. Such agents include TLR agonists, for example polyIC or poly IC 12 U which stimulate TLR3 receptors, most notably on antigen processing cells. The TLR agonist may be given concurrently to 48 hours following antibody administration. Additional immune stimulatory agents include antibodies that promote specific T cell immunity, for example anti-CTLA4 or anti-Transforming Growth Factor-beta dosed concurrent to 48 hours the specific monoclonal antibody infusion with the intent of preventing the counter regulatory dampening of specific T cell immunity being stimulated by the monoclonal IgE.

The methods according to the invention are useful for treating patients having a disease associated with an antigen. As used herein, the term "disease associated with an antigen" means a condition in which signs or symptoms of illness in a majority of patients are present when the antigen is present in the patient's body at a certain concentration, but in which signs or symptoms of illness are absent or reduced when the antigen is absent from the patient's body or present in the patient's body at a lower concentration. "Signs or symptoms of illness" are clinically recognized manifestations or indications of disease. It will be appreciated that a "patient suffering from a disease associated with an antigen" of the invention may not yet be symptomatic for the disease. Accordingly, a patient with circulating CA125 may be is a patient according to the invention even though that patient may not yet be symptomatic for ovarian or endometrial adenocarcinoma; and a patient with elevated PSA may not be symptomatic for prostate cancer. As used herein the terms "treat," "treating" and "treatment" of a disease associated with an antigen (e.g. cancer) includes: inhibiting the onset of disease in a patient; eliminating or reducing tumor burden in a patient; prolonging survival in a patient; prolonging the remission period in a patient following initial treatment with chemotherapy and/or surgery; and/or prolonging any period between remission and relapse in a patient.

The amount of the composition of the invention which will be effective in the treatment, inhibition and prevention of the disease associated with the antigen to which the antibody of the invention is specific and can be determined by standard clinical techniques. In addition, in vitro assays may optionally be employed to help identify optimal dosage ranges. The precise dose to be employed in the formulation will also depend on the route of administration, and the seriousness of the disease or disorder, and should be decided according to the judgment of the practitioner and each patient's circumstances. Effective doses may be extrapolated from dose-response curves derived from in vitro or animal model test systems.

For the therapeutic IgE antibodies of the invention, the dosage administered to a patient is typically 0.001 μg/kg to 1 mg/kg of the patient's body weight. Preferably, the dosage administered to a patient is between 0.01 μg/kg and 0.1 mg/kg of the patient's body weight, more preferably 0.02 μg/kg to 20 μg/kg of the patient's body weight. Generally, the IgE monoclonal antibodies of the invention have a much higher affinity for the Fcϵ R (as compared to IgG antibodies, for example) and longer half-life within the human body than antibodies from other species. Thus, lower dosages of the antibodies of the invention for example as much as 100 times lower than typical doses of IgG therapeutic antibodies and less frequent administration is often possible particularly when combined with one or more relevant bioactivity-enhancing agents in accordance with the methods of the invention.

As discussed above, the inventors have appreciated that the dose of monoclonal IgE that will be effective in both mobilizing direct antibody mediated toxicity against the diseased cells in question and also mobilize T cell mediated cellular immunity against the disease associated antigen cell of origin (such as a tumor cell or other antigen source) are expected to be the same or similar dose and are also expected to be much lower than the dosages required for direct targeting IgG1 antibodies in which doses in the range of 10 mg/kg are required. For patients who have developed treatment preventing immediate hypersensitivity to administered IgG antibodies, the protocol of and experience of Castells demonstrate that a starting dose of 0.034 mg/ml can typically be safely infused as a first dose in a rush desensitization (Castells et al., J. *Allergy Clin. Immunol.* 122:574 (2008), Table 1). For a therapeutic IgE antibody of the invention, a typical therapeutic dose of 1 mg antibody may preferably be infused as a 0.01 mg/mL solution (100 ml total volume), thus the therapeutic dose for a therapeutic IgE antibody of the invention is below the first (and lowest) dose in a rush desensitization protocol of an IgG antibody. The safe administration of monoclonal IgE thus incorporates a substantial safety and dosing margin over a standard protocol for demonstrated limiting hypersensitivity and optionally may include the use of coadministered bioactivity-enhancing agents to assure the safety component of the therapeutic index is acceptable.

In accordance with the methods of the invention, the therapeutic IgE antibody and the bioactivity-enhancing agent are administered simultaneously, in either separate or combined formulations, or sequentially at different times separated by minutes, hours or days, but in some way act together to provide the desired therapeutic response. As used herein, "administering" refers to any action that results in exposing or contacting a composition containing an antibody of the invention and a bioactivity-enhancing agent with a pre-determined cell, cells, or tissue, typically mammalian. As used herein, administering may be conducted in vivo, in vitro, or ex vivo. For example, a composition may be administered by injection or through an endoscope. Administering also includes the direct application to cells of a composition according to the present invention. For example, during the course of surgery, tumor cells may be exposed. In accordance with an embodiment of the invention, these exposed cells (or tumors) may be exposed directly to a composition of the present invention, e.g., by washing or irrigating the surgical site and/or the cells.

In one embodiment, the bioactivity-enhancing agent is administered at least 30 minutes prior to administration of the therapeutic IgE antibody. In one embodiment the bioactivity-enhancing agent is administered at least one week prior to, or one week after, administration of the therapeutic IgE antibody.

In accordance with a method of the invention compositions comprising the therapeutic IgE antibody and compositions comprising the bioactivity-enhancing agent (whether the same or different) may be administered to the patient by any immunologically suitable route. For example, the antibody may be introduced into the patient by an intravenous, subcutaneous, intraperitoneal, intrathecal, intravesical, intradermal, intramuscular, or intralymphatic routes. The composition may be in solution, tablet, aerosol, or multi-phase formulation forms. Liposomes, long-circulating liposomes, immunoliposomes, biodegradable microspheres, micelles, or the like may also be used as a carrier, vehicle, or delivery system. Furthermore, using ex vivo procedures well known in the art, blood or serum from the patient may be removed from the patient; optionally, it may be desirable to purify the antigen in the patient's blood; the blood or serum may then be mixed with a composition that includes a binding agent according to the invention; and the treated blood or serum is returned to the patient. The invention should not be limited to any particular method of introducing the binding agent into the patient.

Administration may be once, more than once, and over a prolonged period. As the compositions of this invention may be used for patients in a serious disease state, i.e., life-threatening or potentially life-threatening, excesses of the binding agent may be administered if desirable. Actual methods and protocols for administering pharmaceutical compositions, including dilution techniques for injections of the present compositions, are well known or will be apparent to one skilled in the art. Some of these methods and protocols are described in Remington's Pharmaceutical Science, Mack Publishing Co. (1982).

In one preferred embodiment, the bioactivity-enhancing agent is a corticosteroid such as cortisol (1 mg/kg). Administration of corticosteroids 8 hours to at least 30 minutes prior to infusion of the therapeutic IgE antibody will prevent life threatening hypersensitivity and not interfere with the ability of the patient to generate an antigen specific T cell response or mediate ADCC or ADCP i.e., generate protective immunity with anti-antigen IgE-antigen immune complexes.

In one preferred embodiment the bioactivity enhancing agent is a human anti-transforming growth factor beta antibody (TGF-beta) administered to prevent a iummune suppressive effect of TGF beta on specific T cell induction with the monoclonal IgE antibody.

In one preferred embodiment, the bioactivity-enhancing agent is docetaxel, cytotoxan and/or gemcitabine for enhancing the immune response of the therapeutic IgE antibody by enhancing specific T cell response and perhaps negatively modulating regulatory T cells.

In one preferred embodiment the bioactivity-enhancing agent is paclitaxel and/or docetaxel in combination with a therapeutic IgE antibody can switch the immune response from Th2 to Th1/Tc1 and enhance the adaptive immune response. Taxanes signal through toll receptor 4 and induce TNF-α and IFN-α, mature the dendritic cells and thus enhance the immune response, especially the Th1 and CTL responses.

In one preferred embodiment the bioactivity-enhancing agent is a TLR3 agonist such as poly IC or polylpolyC12U that trigger TNF-α and IFN-α and IL-6 release in the disease microenvironment, mature local antigen presenting cells to induce more potent cellular immunity, and enhance the direct ADCC/ADCP mediated by the IgE coated effector cells. Timing of TLR administration is concurrent to a window 30 minutes to several hours following antibody administration. The cytokine environment induced by TLR is also likely to further inhibit the tendency for IgE to promote an allergic Th2 driven response as previously observed by Maurer et al (supra). This may also effect safety as such as switch is believed to reduce the chance of hypersensitivity.

In one preferred embodiment the invention provides methods of enhancing the biosafety of an IgE antibody comprising administering the antibody intravenously at a concentration of 0.010 to 0.1 mg/ml at a rate of 1 to 4 ml/min for 30 minutes.

In another preferred embodiment, the invention provides methods of enhancing bioactivity by preadministration of corticosteroid; concurrent administration of a taxane, concurrent to follow up administration of an immune stimulant such as a TLR agonist, CTLA-4 antagonist, TGF beta antagonist; and follow up administration by 2 to 7 days of gemcitabine.

The effectiveness of the methods of the present invention may be monitored in vitro or in vivo. Humoral responses may be monitored in vitro by conventional immunoassays, where the anti-tumor activity of the response may be determined by complement-mediated cytotoxicity and/or antibody-dependent cellular cytotoxicity (ADCC) assays. The assay methodologies are well known, and are described in Handbook of Experimental Immunology, Vol. 2, Blackwell Scientific Publications, Oxford (1986). Other assays may be directed to determining the level of the antigen in the patient or tissue. Cell-mediated immunity may be monitored in vivo by the development of delayed-type hypersensitivity reactions, or other in vivo or in vitro means known to those skilled in the art, including but not limited to the skin test reaction protocol, lymphocyte stimulation assays, measuring the toxicity of a subject's lymphocytes to tumor cells by using a standard cytotoxicity assay, by a limiting dilution assay, or by measuring plasma levels of cytokines using standard ELISA assays.

Determining the effectiveness of the methods of the invention may also be accomplished by monitoring cell killing. Those skilled in the art will recognize that there are a variety of mechanisms that are proof of cell killing. Cell killing may be demonstrated by showing ADCC, CDC, the production of natural killer (NK) cells, and/or that cytotoxic T lymphocytes (CTLs) are produced.

EXAMPLES

Example 1

Figure 2:
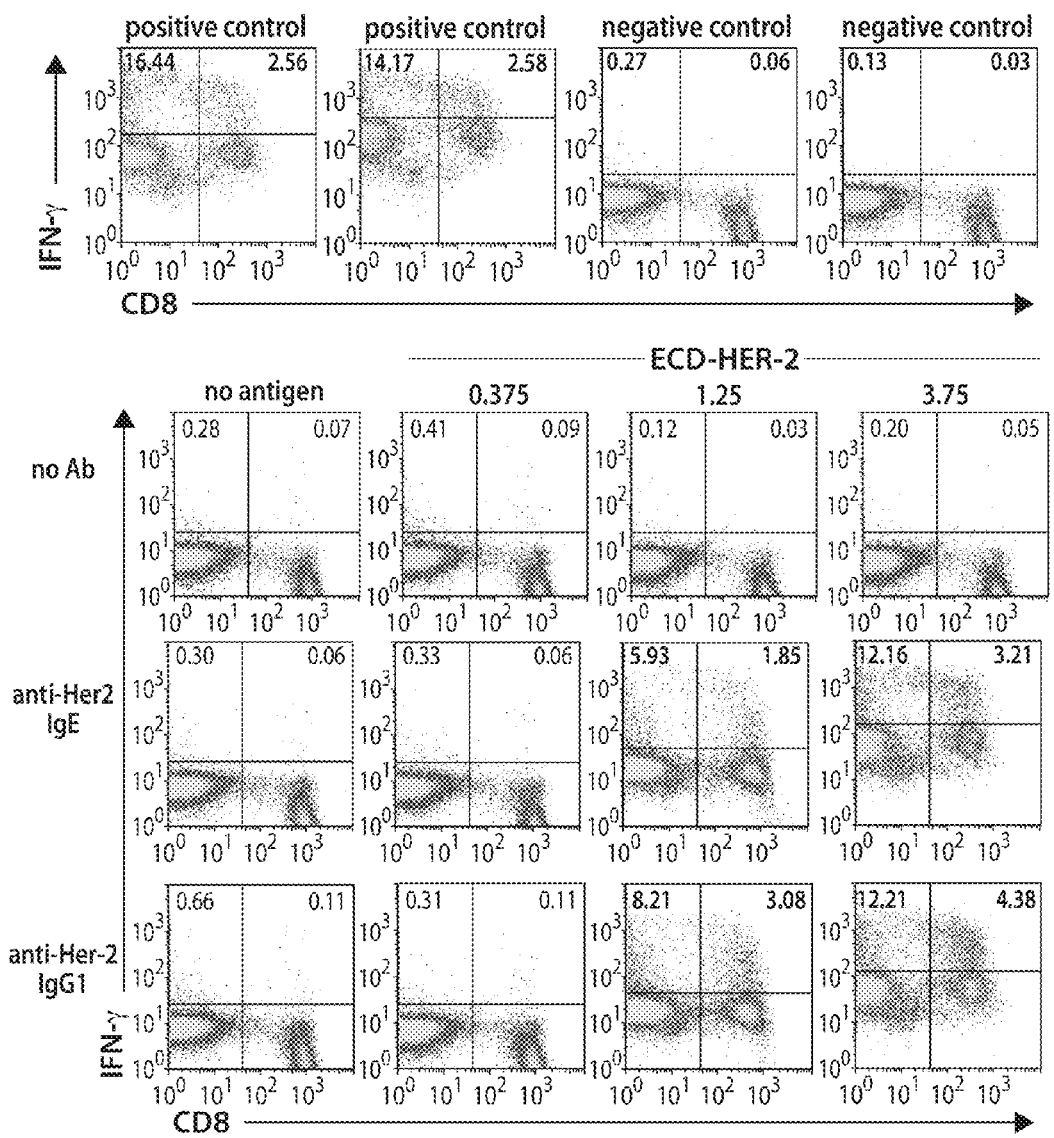
FIG. 2: antigen presentation is enhanced by anti-Her2 IgE and IgG1 Abs. T cells from APA assay were analyzed for IFN-γ production by intracellular cytokine staining and flow cytometry. T cells from the APA were stained with anti-CD3-FITC and anti-CD8-PECy5 and then permeabilized and stained with anti-IFNγ-PE. Plots are gated on CD3 (FITC) positive cells and show IFN-γ vs CD8 staining The top panel is plots of T cells stimulated with PMA and ionomycin (positive control) or T cells left in media alone (negative control). The bottom panel includes plots of T cells that were stimulated in the APA with ECD-Her2 alone (no Ab) or with anti-Her-2 IgE or anti-Her2 IgG1.
Figure 3:
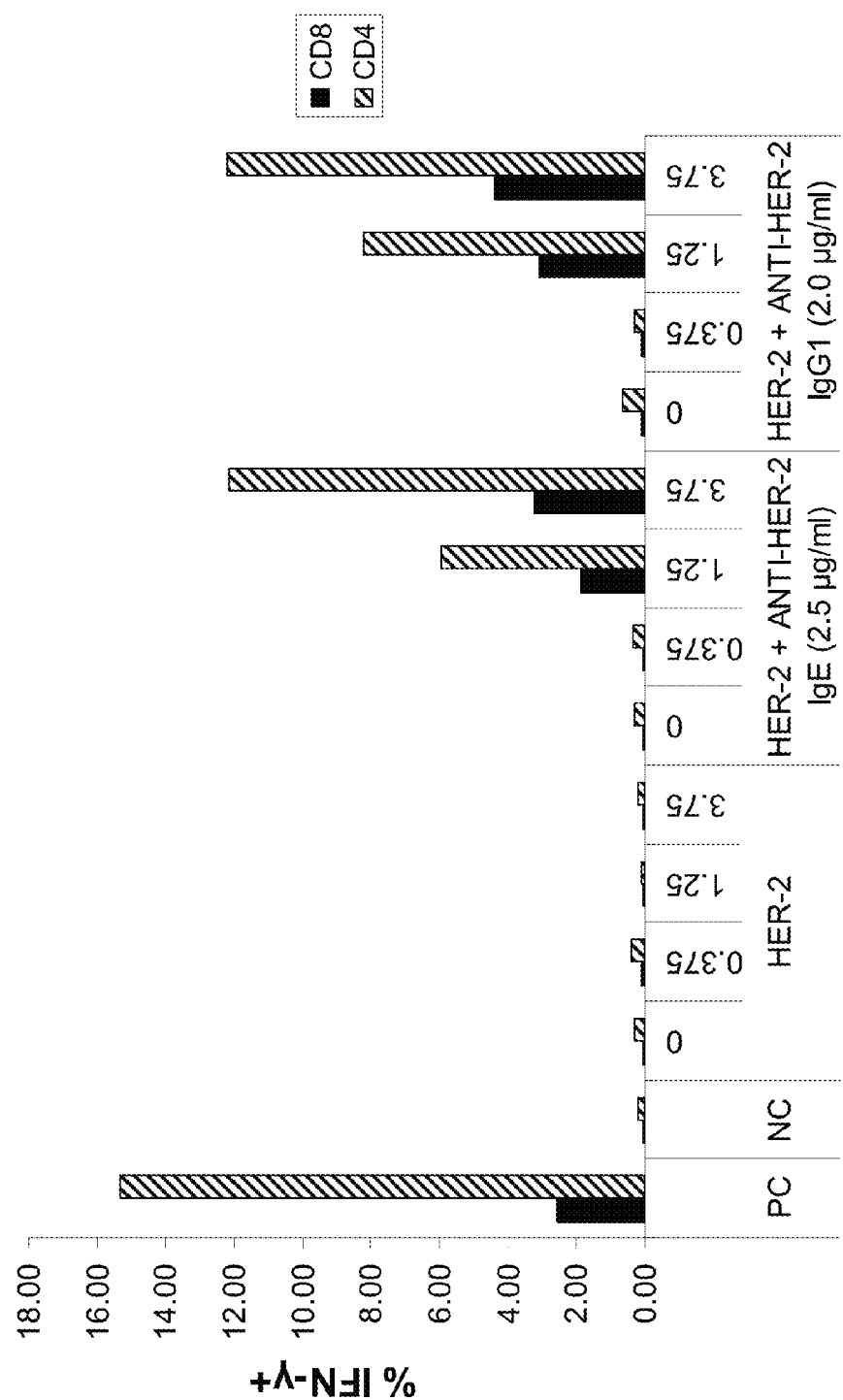
FIG. 3: antigen presentation is enhanced by anti-Her2 IgE and IgG1 Abs. Bar graph of the results of the antigen presentation assay with anti-HER-2 IgE and anti-HER-2 IgG1. Values are the percentage of CD8+ and CD8-(CD4+) cells within the live CD3+ gate that are positive for intracellular IFN-γ staining.
Figure 4:
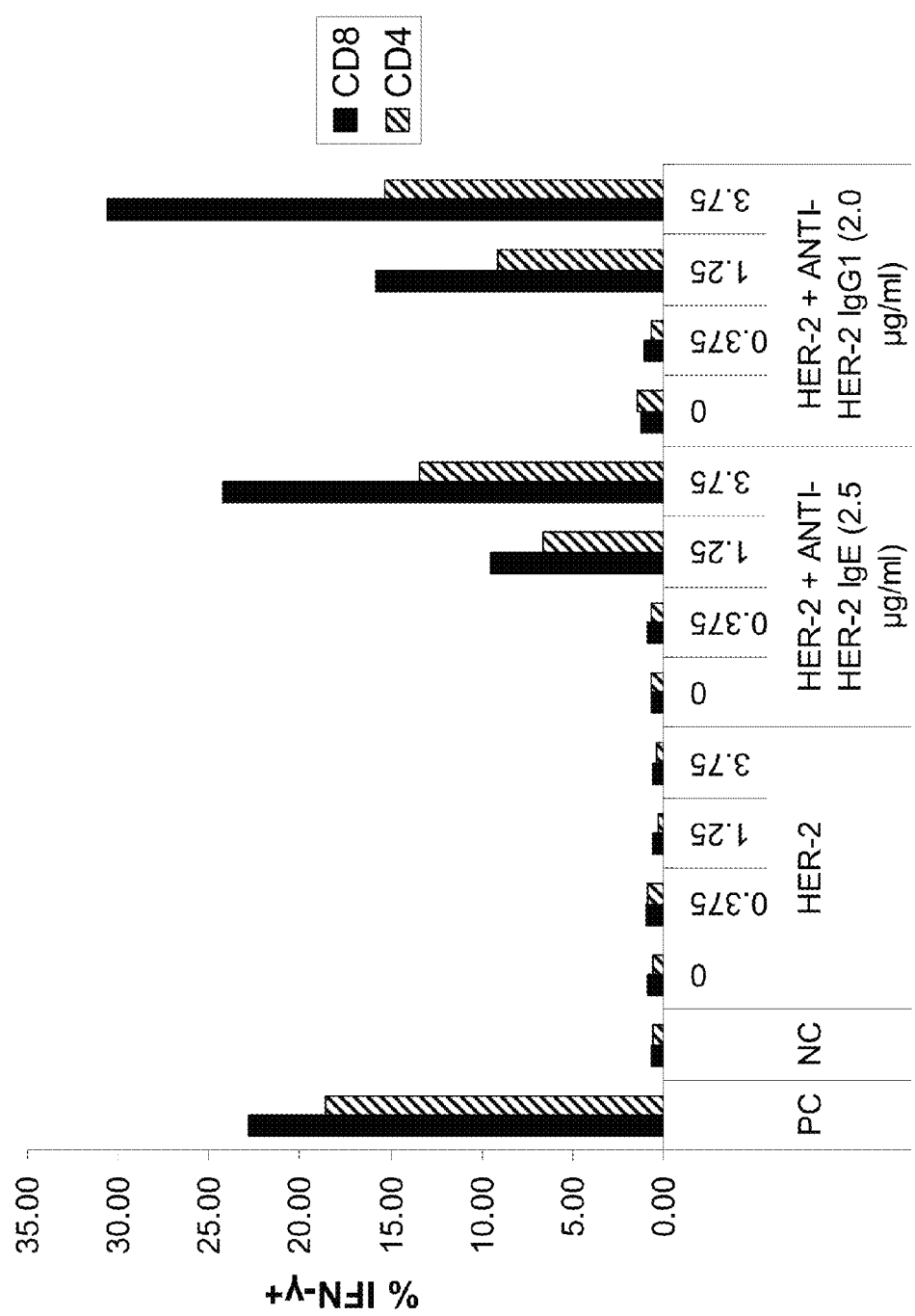
FIG. 4: Antigen presentation is enhanced by anti-Her2 IgE and IgG1 Abs. Bar graph of the results of the antigen presentation assay with anti-HER-2 IgE and anti-HER-2 IgG1. Values are the percentage of CD8+ and CD8-(CD4+) cells within either the live CD3+ CD8+ gate or the live CD3+ CD8-(CD4+) gate that are positive for intracellular IFN-γ staining.
Figure 5:
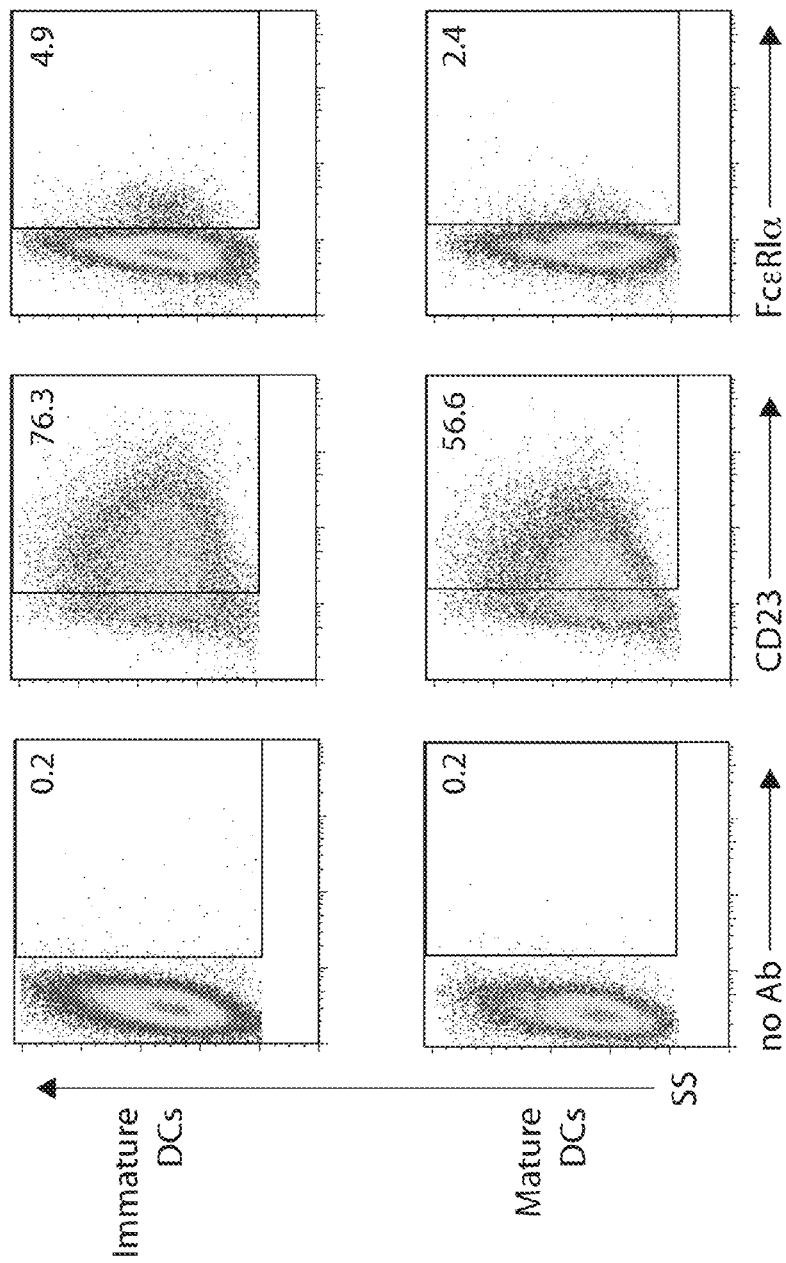
FIG. 5: FcεR expression on cultured DCs. Immature and mature DCs were stained with a PE-labeled anti-Fc epsilon RIalpha Ab (clone AER-37, eBioscience) or a PE-labeled anti-Fc epsilon RII (CD23) Ab (clone M-L233, BD Pharmingen) and analyzed by flow cytometry. Flow plots are side scatter (SSC) vs. FL-2 (PE).

Use of Monoclonal IgE to Induce a T Cell Immune Response Rich in $CD8^+$ Ifn-$\gamma$ Producing T Cells Human dendritic cells (DC) are cultured from human PBMCs in the presence of IL-4 and GM-CSF as previously described (Berlyn 2001) and illustrated in FIG. 1. On day 7, the primary culture is loaded with tumor associated antigen (TAA) and antibody (Ab) and matured with a standard maturation cocktail (e.g. TNF-$\alpha$/IFN-$\alpha$). The culture is then combined with autologous lymphocytes and cultured for 7 days. Subsequently, the lymphocyte culture is stimulated with two additional rounds of TAA/Ab using fresh dendritic cells cultures as illustrated. Following the third round of TAA/Ab stimulation, the lymphocytes are treated with Brefeldin A, which prevents the secretion of synthesized cytokine. The next day, cells are harvested and stained extracellularly with anti-CD3-FITC and anti-CD8-PE-Cy5. Cells are then washed, fixed, and permeabilized and stained intracellularly with anti-IFN-$\gamma$-PE and analyzed by flow cytometry. The $CD8^+$ IFN-$\gamma$ producing population is defined as $CD3^+$ $CD8^+$ IFN-$\gamma^+$ and the $CD4^+$ IFN-$\gamma$ producing population is defined as $CD3^+$ $CD8^-$ IFN-$\gamma^+$. A representative experiment using an anti-Her2 IgE, an anti-Her2 IgG1 (Herceptin) and Her2 protein is illustrated in FIG. 2. Antigen presentation is enhanced by anti-Her2 IgE and IgG1 Abs. T cells from APA assay were analyzed for IFN-$\gamma$ production by intracellular cytokine staining and flow cytometry. T cells from the APA were stained with anti-CD3-FITC and anti-CD8-PECy5 and then permeabilized and stained with anti-IFN-$\gamma$-PE. Plots are gated on CD3 (FITC) positive cells and show IFN-$\gamma$ vs CD8 staining The top panel is plots of T cells stimulated with PMA and ionomycin (positive control) or T cells left in media alone (negative control). The bottom panel includes plots of T cells that were stimulated in the APA with ECD-Her2 alone (no Ab) or with anti-Her-2 IgE or anti-Her2 IgG1. Quantification of the effect of the antibody antigen combinations tested in FIG. 2 are illustrated in FIG. 3, and FIG. 4. The T cell response to Her2 is normally minimal; however processing of the immune complex with anti-Her2 IgG1 or anti-er2 IgE results in a stimulation of antigen specific T cell immunity with a enhancement of both CD4 and CD8 IFN gamma phenotypes. Notably IgE to this self antigen induces a potent Tc1 response in contrast to the teachings of the literature based on studies of allergy. The dose of antigen and antibody is optimal at slight antibody excess and is similar for IgE mediated primarily through dendritic cells Fc$\epsilon$RII (CD23), as demonstrated via flow cytometric analysis of an immature and mature in vitro generated DC population (see FIG. 5) and IgG mediated through Fc$\gamma$ receptors. In the illustrated experiment, monoclonal IgE and monoclonal IgG induced a similar pattern of IFN-$\gamma$ specific T cell immunity that was not induced by Ag alone, illustrating the state of tolerance typically encountered to self- and tumor-Ags.

Example 2

Use of Monoclonal Human IgE to Induce Immediate Hypersensitivity Using Human Whole Leukocyte Fraction and RBL-Sx-38 Cells An in vitro demonstration of the potential of tumor cells to induce a local allergic reaction is illustrated using a monoclonal anti-Her2 human IgE with SKBR3 human breast cancer cells or purified Her-2 protein in conjunction with human fresh leukocyte fraction (targets) incubated with PBMC or RBL-Sx-38 cells, a rat basophilic leukemia cell line developed and containing a functional alpha chain to the human Fc$\epsilon$RI (effectors). Tumor cells are incubated with increasing concentrations of Her-2 specific IgG or IgE and combined with the effector cells. Evidence of local effector cell activation is measured by assessing histamine and or beta hexosimimidase release into the culture supernatant. Confirmatory experiments showing specificity for the Her-2 Ag can be conducted using anti-NP IgE and NP-HSA or anti-PSA IgE and PSA or conjugated PSA. In addition to immediate hypersensitivity, the target cells can be pre-labeled with Calcein AM and the ability of the anti-Her2 IgE or IgG to induce tumor killing can be monitored via direct effect of the PBMC or the RBL-Sx-38 cells in inducing release of the Calcein AM label.

Example 3

Augmentation of Direct Tumor Targeting

Having established the baseline activity of a representative Ag specific IgE monoclonal in terms of both histamine release and basic tumor cell killing, the effect of corticosteroid and specific adjuvant on the model can be measured. It will be demonstrated that corticosteroid does not prevent histamine release; however, it may modestly diminish the amount of cell killing observed in the assay. The ability of TLR3 stimulation to augment the ADCC effect is addressed by adding low concentrations (1 to 25 µg/ml) of poly IC (Sigma) to the system at various time points. The data will reveal that addition of poly IC 30 minutes to 4 hours post co-incubation enhances the amount of killing observed.

Example 4

Human FcεRI Transgenic Mice Receive Intradermal Injection of Tumor Microspheroids Passive cutaneous anaphylaxis is performed in transgenic mice expressing the human FcεRIα. Transgenic mice are shaved and injected intradermally in different regions of the dorsal side with 50 μA of 6 mg/ml histamine base (Hollister-Stier, Spokane, Wash.), 1 μg anti-PSA IgE, CT26-PSA or CT26-Neo microspheroid alone, 2 μg of crosslinker anti-human kappa antibody alone, 1 μg anti-PSA IgE plus CT26-PSA or CT26-Neo microspheroid, or 1 μg anti-PSA IgE crosslinked with 2 μg of an anti-human kappa antibody. After 15 min, 1% Evans Blue in 250 μA saline is injected i.v. Mice are sacrificed 20 min later, and local cutaneous anaphylaxis is assessed visually by the blue leakage in the area surrounding the injection. In the presence of IgE specific for the tumor cell line; immediate wheal and flare reactions are seen at the site of the tumor injection, but not in the presence of an antigen specific IgG antibody or isotype controls. This effect is not prevented by administration of cortisol to the mouse; however pre-administration of an H1 blocking agent inhibits the size of the response.

Example 5

Using Corticosteroid to Prevent Systemic Anaphylaxis Associated with Monoclonal IgE Administration Macaque monkeys have an FcεR that recognizes human IgE and the effector cells it is expressed on is similar to those in humans. In this experiment, Macaque monkeys will be dosed with increasing concentrations of anti-Her-2 IgE to achieve serum concentrations up to 10 μg/ml. Skin test reactivity to Her-2 protein or glutaraldeyhyde agglutinated Her-2 protein will be measured by intradermal skin testing. Administration of complexed Her-2 is expected to induce some signs of systemic hypersensitivity in the treated monkeys however premedication with 1 mg/kg cortisone will prevent evidence of systemic anaphylaxis in the monkeys receiving the infusion of the IgE targeted protein.

Example 6

Tumor Control Studies

The ability to measure anti-tumor immunity with the human specific IgE monoclonals in animal models is complicated by the lack of binding of rodent FcεR to human IgE. In addition to the lack of binding, mice also see human IgE as a foreign protein and therefore would most likely mount an immune response against it causing its elimination before it could be effective in an anti-tumor response. Finally, in order to perform human tumor studies in mice, the mice also have to be tolerant to the human tumor antigen. In order to circumvent these obstacles, triple transgenic mice that express the human FcεRIα chain, human IgE, and the human tumor antigen of interest (ie. PSA, Her-2) are generated. BALB/c mice that express the FcεRIα chain have been generated and it has been shown that these mice can bind human IgE via the FcεRI (Dombrowicz, et al., J Immunol 157:1645-51 (1996)). BALB/c transgenic mice expressing human IgE, human Her-2 and human PSA are available for cross-breeding to the human FcεRIα transgenic mice. Pups would need to be tested for the presence of the transgene to all relevant genes (FcεRIα, human IgE, and PSA or Her-2). After several round of cross-breeding, triple positive mice are then selected for immunization experiments in which murine tumor cell lines (such as CT-26 PSA or SKBR3) containing the human tumor antigen are injected subcutaneously in the mice. Tumor cell growth is measured in the absence of antigen specific monoclonal, or in the face of increasing concentrations of antibody. The ability of TLR stimulation and/or chemotherapeutic agents, as well as distinct timing of doses of antibody (Ab) and/or pharmacologic agent, and their effect on the anti-tumor activity in immunized rodents will also be assessed. Analysis of control of tumor size and in animal mortality can be used as endpoints.

The patent and scientific literature referred to herein establishes the knowledge that is available to those with skill in the art. All United States patents and published or unpublished United States patent applications cited herein are incorporated by reference. All published foreign patents and patent applications cited herein are hereby incorporated by reference. All other published references, documents, manuscripts and scientific literature cited herein are hereby incorporated by reference.

While this invention has been particularly shown and described with references to preferred embodiments thereof, it will be understood by those skilled in the art that various changes in form and details may be made therein without departing from the scope of the invention encompassed by the appended claims. It will also be understood that none of the embodiments described herein are mutually exclusive and may be combined in various ways without departing from the scope of the invention encompassed by the appended claims.

What is claimed is:

1. A method for treating cancer in a human patient comprising administering to the patient a therapeutic IgE antibody in combination with at least one immunostimulatory compound wherein the immunostimulatory compound is a TLR3 agonist or a TLR4 agonist; and at least one immunosuppressive agent wherein the immunosuppressive agent is a corticosteroid and optionally in further combination with a chemotherapeutic agent wherein the chemotherapeutic agent is gemcitabine, cyclophosphamide, topotecan, or doxorubicin, wherein the IgE antibody is a monoclonal antibody comprising human Fc epsilon (ε) constant regions and a variable region comprising at least one antigen binding region specific for a cancer antigen and wherein the immunosuppressive agent is administered to the patient at least 30 minutes prior to administration of the therapeutic IgE antibody.

2. The method of claim 1, wherein the IgE antibody is a chimeric antibody, a humanized antibody or a fully human antibody.

3. The method of claim 1, wherein the immunosuppressive agent is administered to the patient about 30 minutes to about 8 hours prior to administration of the therapeutic IgE antibody.

4. The method of claim 1, wherein the patient's Th1-type immune response to the antigen is enhanced as compared to the administration of the therapeutic IgE antibody alone.

5. The method of claim 1, wherein the patient's cytotoxic T-lymphocyte response to the antigen is enhanced as compared to the administration of the therapeutic IgE antibody alone.

6. A method for treating a tumor in a human patient comprising administering to the patient a therapeutic IgE antibody specific for an antigen associated with the tumor in combination with at least one immunosuppressive agent wherein the immunosuppressive agent is a corticosteroid and at least one immunostimulatory compound wherein the immunostimulatory compound is a TLR3 agonist or a TLR4 agonist and optionally in further combination with a chemotherapeutic agent wherein the chemotherapeutic agent is gemcitabine, cyclophosphamide, topotecan, or doxorubicin, wherein the therapeutic IgE antibody is a monoclonal antibody comprising human Fc epsilon ($\epsilon$) constant regions and wherein the immunosuppressive agent is administered to the patient at least 30 minutes prior to administration of the therapeutic IgE antibody.

7. The method of claim 6, wherein the therapeutic IgE antibody is a chimeric antibody; a humanized antibody, and a fully human antibody.

8. The method of claim 6, comprising administering a chemotherapeutic agent selected from the group consisting of gemcitabine, cyclophosphamide, topotecan, or doxorubicin.

* * * * *